US008337879B2

(12) United States Patent
Kronenthal

(10) Patent No.: US 8,337,879 B2
(45) Date of Patent: *Dec. 25, 2012

(54) ABSORBABLE IMPLANTS AND METHODS FOR THEIR USE IN HEMOSTASIS AND IN THE TREATMENT OF OSSEOUS DEFECTS

(75) Inventor: Richard L. Kronenthal, Fair Lawn, NJ (US)

(73) Assignee: ORTHOCON, Inc., Irvington, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/087,584

(22) Filed: Apr. 15, 2011

(65) Prior Publication Data

US 2011/0189304 A1    Aug. 4, 2011

Related U.S. Application Data

(63) Continuation of application No. 11/224,650, filed on Sep. 12, 2005, now Pat. No. 7,955,616, and a continuation-in-part of application No. 10/941,890, filed on Sep. 16, 2004, now Pat. No. 8,105,628.

(60) Provisional application No. 60/628,989, filed on Nov. 18, 2004, provisional application No. 60/504,978, filed on Sep. 23, 2003.

(51) Int. Cl.
*A61F 2/02* (2006.01)

(52) U.S. Cl. ...................................... 424/426

(58) Field of Classification Search .................. None
See application file for complete search history.

(56) References Cited

U.S. PATENT DOCUMENTS

| 2,611,706 A | 9/1952 | Bernhart et al. |
|---|---|---|
| 2,642,375 A | 6/1953 | Henderson et al. |
| 2,772,999 A | 12/1956 | Masci et al. |
| 2,773,000 A | 12/1956 | Masci et al. |
| 3,109,562 A | 11/1963 | Ferris |
| 3,924,000 A | 12/1975 | Thiele et al. |
| 4,186,448 A | 2/1980 | Brekke |
| 4,439,420 A | 3/1984 | Mattei et al. |
| 4,443,430 A | 4/1984 | Mattei et al. |
| 4,503,034 A | 3/1985 | Maupetit et al. |
| 4,568,536 A | 2/1986 | Kronenthal et al. |
| 4,588,583 A | 5/1986 | Pietsch et al. |
| 4,650,665 A | 3/1987 | Kronenthal et al. |
| 4,770,803 A | 9/1988 | Forsberg |
| 5,047,166 A | 9/1991 | Weil |
| 5,073,373 A | 12/1991 | O'Leary et al. |
| 5,108,403 A | 4/1992 | Stern |
| 5,143,730 A | 9/1992 | Fues et al. |
| 5,284,655 A | 2/1994 | Bogdansky et al. |
| 5,290,558 A | 3/1994 | O'Leary et al. |
| 5,308,623 A | 5/1994 | Fues et al. |
| 5,314,476 A | 5/1994 | Prewett et al. |
| 5,356,629 A | 10/1994 | Sander et al. |
| 5,405,366 A | 4/1995 | Fox et al. |
| 5,482,717 A | 1/1996 | Fues et al. |
| 5,484,601 A | 1/1996 | O'Leary et al. |
| 5,496,819 A | 3/1996 | Okuyama et al. |
| 5,552,454 A | 9/1996 | Kretschmann et al. |
| 5,641,502 A | 6/1997 | Skalla et al. |
| 5,681,873 A | 10/1997 | Norton et al. |
| 5,696,101 A | 12/1997 | Wu et al. |
| 5,730,967 A | 3/1998 | Hill et al. |
| 5,776,193 A | 7/1998 | Kwan et al. |
| 5,785,993 A | 7/1998 | Baker et al. |
| 6,030,635 A | 2/2000 | Gertzman et al. |
| 6,117,444 A | 9/2000 | Orgill et al. |
| 6,139,872 A | 10/2000 | Walsh |
| 6,162,241 A | 12/2000 | Coury et al. |
| 6,174,422 B1 | 1/2001 | Honig et al. |
| 6,174,442 B1 | 1/2001 | Geisser et al. |
| 6,281,195 B1 | 8/2001 | Rueger et al. |
| 6,331,313 B1 | 12/2001 | Wong et al. |
| 6,383,502 B1 | 5/2002 | Dunshee et al. |
| 6,413,539 B1 | 7/2002 | Shalaby |
| 6,420,454 B1 | 7/2002 | Wenz et al. |
| 6,426,332 B1 | 7/2002 | Rueger et al. |
| 6,437,018 B1 | 8/2002 | Gertzman et al. |
| 6,454,787 B1 | 9/2002 | Maddalo et al. |
| 6,458,375 B1 | 10/2002 | Gertzman et al. |
| 6,485,749 B1 | 11/2002 | Shalaby |
| 6,565,884 B2 | 5/2003 | Nimni |
| 6,576,249 B1 | 6/2003 | Gendler et al. |
| 6,764,517 B2 | 7/2004 | Yamamoto et al. |
| 6,902,584 B2 | 6/2005 | Kwan et al. |
| 6,911,212 B2 | 6/2005 | Gertzman et al. |

(Continued)

FOREIGN PATENT DOCUMENTS

EP            0537559         4/1993

(Continued)

OTHER PUBLICATIONS

Jain et al. Clinica Chimica Acta, 224: 97-103 (1994).
Murohara, T., et al., "*Inhibition of platelet adherence to mononuclear cells by α-Tocopherol of P-Selectin*" Circulation 141-148 (2004).
Onodera, S. et al. "*Macrophage migration inhibitory factor induces phagocytosis of foreign particles by macrophages in autocrine and paracrine fashion*". Immunology 92:131-137 (1997).
Rodriguez et al. "*Toxicology of Polyalkylene Block Copolymers.*" Nonionic Surfactants. Nace ed. New York: Marcel Dekker, Inc. 228-229 (1996).
Steiner, M. et al., "*Vitamin E: An inhibitor of the platelet release reaction*" J. Clin. Inv. 57:732-737 (1976).
Tang, L. et al., "*Natural responses to unnatural materials: A molecular mechanism for foreign body reactions*". Molecular Medicine 5:351-358 (1999).
Technical Bulletin Pluronic® F68 2004.
Technical Bulletin Pluronic® L35 2004.
Technical Bulletin Pluronic® L121 2004.

(Continued)

*Primary Examiner* — Carlos Azpuru
(74) *Attorney, Agent, or Firm* — Mintz Levin Cohn Ferris Glovsky and Popeo, P.C.; Ivor R. Elrifi; Muriel Liberto, Esq.

(57) ABSTRACT

The present invention relates to mechanically hemostatic body-absorbable compositions having a putty-like consistency. The compositions preferably comprise a finely powdered, carboxylic acid salt and a liquid block copolymer of ethylene oxide and propylene oxide.

21 Claims, No Drawings

U.S. PATENT DOCUMENTS

| | | |
|---|---|---|
| 6,916,788 B2 | 7/2005 | Seo et al. |
| 6,949,251 B2 | 9/2005 | Dalal et al. |
| 6,960,346 B2 | 11/2005 | Shukla et al. |
| 7,074,425 B2 | 7/2006 | Constantine et al. |
| 7,553,913 B2 | 6/2009 | Wellisz et al. |
| 7,771,755 B2 | 8/2010 | Li et al. |
| 7,829,616 B2 | 11/2010 | Wellisz et al. |
| 7,842,097 B2 | 11/2010 | Yamamoto et al. |
| 8,048,443 B2 | 11/2011 | Benedict et al. |
| 8,048,857 B2 | 11/2011 | McKay et al. |
| 8,105,628 B2 * | 1/2012 | Kronenthal .................. 424/484 |
| 2002/0048551 A1 | 4/2002 | Keller et al. |
| 2002/0076429 A1 | 6/2002 | Wironen et al. |
| 2002/0090398 A1 | 7/2002 | Dunn et al. |
| 2002/0102301 A1 | 8/2002 | Schwarz |
| 2003/0008011 A1 | 1/2003 | Mershon |
| 2003/0049326 A1 | 3/2003 | Nimni |
| 2003/0093157 A1 | 5/2003 | Casares et al. |
| 2003/0095945 A1 | 5/2003 | Levy et al. |
| 2003/0153528 A1 | 8/2003 | Levinson |
| 2004/0018238 A1 | 1/2004 | Shukla |
| 2004/0109893 A1 | 6/2004 | Chen et al. |
| 2005/0037088 A1 | 2/2005 | Pendharkar et al. |
| 2005/0065214 A1 | 3/2005 | Kronenthal |
| 2005/0113341 A1 | 5/2005 | Timmer et al. |
| 2005/0153869 A1 | 7/2005 | Connor et al. |
| 2006/0002976 A1 | 1/2006 | Kronenthal |
| 2006/0013857 A1 | 1/2006 | Kronenthal |
| 2006/0067971 A1 | 3/2006 | Story et al. |
| 2006/0067973 A1 | 3/2006 | Schachter |
| 2006/0280801 A1 | 12/2006 | Kronenthal |
| 2007/0191963 A1 | 8/2007 | Winterbottom et al. |
| 2009/0048145 A1 | 2/2009 | Hellerbrand et al. |
| 2009/0143830 A1 | 6/2009 | Bourgeois et al. |
| 2010/0070049 A1 | 3/2010 | O'Donnell et al. |
| 2011/0027332 A1 | 2/2011 | Benedict et al. |
| 2011/0038938 A1 | 2/2011 | Ison et al. |
| 2012/0027817 A1 | 2/2012 | Kronenthal |

FOREIGN PATENT DOCUMENTS

| | | | |
|---|---|---|---|
| EP | 0747072 | A2 | 12/1996 |
| EP | 1010436 | A1 | 6/2000 |
| EP | 1142597 | A1 | 10/2001 |
| GB | 1584080 | | 2/1981 |
| GB | 1584080 | A | 2/1981 |
| KR | 20000005150 | A | 1/2000 |
| WO | 92/21744 | A2 | 12/1992 |
| WO | WO 95/22360 | | 8/1995 |
| WO | WO 96/39995 | | 12/1996 |
| WO | WO-9714376 | A1 | 4/1997 |
| WO | 97/33959 | A1 | 9/1997 |
| WO | WO-9834655 | A1 | 8/1998 |
| WO | 00/45867 | A1 | 8/2000 |
| WO | WO 00/45867 | A1 | 8/2000 |
| WO | WO-0132101 | A1 | 5/2001 |
| WO | WO-0145742 | A1 | 6/2001 |
| WO | WO 01/76649 | | 10/2001 |
| WO | WO-0244276 | A2 | 6/2002 |
| WO | WO-0245686 | A2 | 6/2002 |
| WO | WO-02070029 | A2 | 9/2002 |
| WO | WO-03071991 | A1 | 9/2003 |
| WO | WO-2005025595 | A2 | 3/2005 |
| WO | 2005/034726 | A2 | 4/2005 |
| WO | WO 2005/034726 | A2 | 4/2005 |
| WO | WO-2005120595 | A2 | 12/2005 |
| WO | 2007/014210 | A2 | 2/2007 |
| WO | WO 2007/014210 | A2 | 2/2007 |
| WO | 2005/034726 | A3 | 5/2007 |
| WO | WO 2005/034726 | A3 | 5/2007 |
| WO | WO-2007084725 | A2 | 7/2007 |
| WO | WO-2007107012 | A1 | 9/2007 |
| WO | 2007/014210 | A3 | 10/2007 |
| WO | WO 2007/014210 | A3 | 10/2007 |
| WO | WO-2008079672 | A2 | 7/2008 |
| WO | WO-2009105614 | A2 | 8/2009 |
| WO | WO-2010129099 | A1 | 11/2010 |
| WO | WO-2011005510 | A2 | 1/2011 |
| WO | WO-2011009635 | A1 | 1/2011 |

OTHER PUBLICATIONS

Wang et al., "*A New Pluronic-based Bone Hemostatic Agent that Does Not Impair Osteogenesis*" *Neurosurgery* 49(4): 962-968 (2001).

International Preliminary Report, Application No. PCT/US2006/028823, Date of Issuance: Jan. 29, 2008.

International Preliminary Report, Application No. PCT/US2004/026738, Date of Issuance: Apr. 3, 2007.

Supplementary European Search Report, Application No. EP04781435.5, Mail Date: Jul. 17, 2009.

Examination Report, Application No. EP04781435.5, Mail Date: Nov. 24, 2009.

New Zealand Examination Report, Application No. NZ 563557, Date: Nov. 13, 2009.

Examination Report, Application No. AU2004279319, Date Jul. 15, 2009.

Chinese Office Action, Application No. CN 200480027547.5, Date: Sep. 25, 2009.

Examination Report, Application No. EP 04781435.5, Date: Nov. 24, 2009.

* cited by examiner

ABSORBABLE IMPLANTS AND METHODS FOR THEIR USE IN HEMOSTASIS AND IN THE TREATMENT OF OSSEOUS DEFECTS

CROSS REFERENCE TO RELATED APPLICATIONS

This application is a continuation of U.S. Nonprovisional Patent Application Ser. No. 11/224,650, filed Sep. 12, 2005 now U.S. Pat. No. 7,955,616, which claims priority from U.S. Provisional Application No. 60/628,989 filed Nov. 18, 2004 and is a continuation-in-part of U.S. Patent Application Ser. No. 10/941,890 filed Sep. 16, 2004 now U.S. Pat. No. 8,105,628 which claims priority from U.S. Provisional Application No. 60/504,978 filed Sep. 23, 2003. All patents and patent applications in this paragraph are hereby fully incorporated by reference in their entirety.

STATEMENT REGARDING FEDERALLY SPONSORED RESEARCH OR DEVELOPMENT (Not Applicable)

REFERENCE TO A SEQUENCE LISTING, A TABLE, OR A COMPUTER PROGRAM LISTING APPENDIX SUBMITTED ON COMPACT DISC (SEE 37 CFR 1.52(e)(5))

(Not Applicable)

BACKGROUND OF THE INVENTION

1. Field of the Invention

The invention relates to the management, treatment, therapy, and beneficial control of osseous conditions such as hemorrhage and defects, through the use of materials having various viscosities, cohesive strengths, and consistencies, most particularly putty-like materials as well as creams, pastes, ointments, lotions, and gels. More particularly, various novel, surgically implantable, absorbable formulations, which may contain absorption accelerants, bone growth-inducing materials, anti-infective or anti-neoplastic agents to reduce the risk of infection or tumor growth, respectively, analgesics, anti-inflammatory agents, clot-inducing agents such as vasoconstrictors and styptic materials, are used as bone hemostatic devices and/or as bone healing or therapeutic adjuvants. The compositions also may contain radiopaque materials and colorants.

2. Description of Related Art

Cancellous and cortical bone contains relatively vascular tissues that bleed when their vasculature is disrupted. Thus, when bone is surgically incised or fractured traumatically, e.g., in open or compound fractures, there are at least two major issues which must be medically resolved. The first of these is the occurrence of osseous hemorrhage. When osseous hemorrhage ensues, it must be stopped or effectively controlled (hemostasis) to prevent adverse surgical consequences. The second issue is that of bone growth to promote healing (osteogenesis) of the traumatized bone. Common procedures in which bone is surgically cut include open-heart surgery involving the splitting of the sternum, orthopedic and spinal surgery including hip implants, neurosurgery involving spine or cranial incisions, amputations, trauma treatment, and many other procedures.

At the present time, bone hemostasis is achieved by one or more of (i) manually impregnating the bleeding surface with commercially available, non-absorbable "bone wax", (ii) the use of various hemostatic agents such as oxidized cellulose or microcrystalline collagen and (iii) electrocautery. None of these techniques promotes osteogenesis to any significant extent. In addition to the unmet need for an effective, rapidly absorbable bone hemostatic material, there is also a surgical need for materials to fill bone defect voids and promote healing in such cavities. A variety of paste-like materials, presently available to the surgeon for this purpose, most commonly are based upon coarsely powdered, demineralized allogeneic bone, suspended in a suitable, biocompatible vehicle. These compositions are designed for inducing osteogenesis and healing in the defect but, because of their consistency, non-cohesiveness and other physical attributes of their composition, they do not reliably adhere to injured bone and are not effective hemostatic agents.

There are two major bodies of prior art concerned with bone hemostasis and bone healing, respectively. As discussed below, up to the present time, in the main, only products based upon plasticized non-absorbable waxes have been available to the surgeon for bone hemostasis. The disadvantages of makeshift devices employing, for example, oxidized cellulose as well as the tissue-destructive use of electrocautery (discussed below) are not satisfactory alternatives.

The first body of art is directed specifically to bone waxes which are manually pressed into the pores of the bleeding bone surface, act as an effective mechanical tamponade, and prevent blood from escaping. Presently available bone waxes consist of mixtures of non-absorbable components such as bee's wax, paraffin, petrolatum, fatty ester plasticizers, and the like. These products must be warmed before use and become soft, kneadable and spreadable by the surgeon onto and into cut bone surfaces. Because available bone waxes are not absorbable and reside indefinitely where they are placed by the surgeon, they act as permanent physical barriers that inhibit osteogenesis, thereby preventing or slowing bone healing. In addition, such a site acts as a perpetual postoperative nidus for infection. If such infection does occur, it is usually chronic and difficult to treat using conventional anti-infective therapy and re-operation, to surgically excise the infected site, often becomes necessary. For these reasons, commercially available bone waxes do not enjoy widespread orthopedic use.

Other products or techniques used in this application include oxidized cellulose products indicated for soft tissue hemostasis, e.g., Surgicel®, which are absorbable and would not be expected to induce the complications cited above for bone wax. However, they are not effective hemostatic products for bone because of their inappropriate physical form (knitted fabric) and are too difficult to use effectively on cut bone because of lack of adherence within the bone pores.

The use of electrocautery, which thermally sears oozing blood vessels closed, is time-consuming and produces widespread tissue damage which may delay osteogenesis as well as allow soft tissue in-growth that interferes with normal bone union, presenting difficult problems for orthopedic surgeons in general and spine surgeons in particular.

Collagen in various forms, alone or in combination with fibrin and suspended in various delivery vehicles has been proposed as a bone hemostatic agent but problems with, for example, storage stability, cohesiveness, and biocompatibility have prevented practical fruition.

The adaptation of synthetic absorbable polymers to this application has not succeeded, apparently because of technical difficulties in suitably formulating hydrolytically unstable synthetic absorbable polymers into practical products with reasonable package shelf life, useful handling properties and acceptable biocompatibility and absorption rates.

The second body of prior art primarily is concerned with bone healing and the treatment of bone defects. The bone healing prior art compilation primarily describes the development of biocompatible, absorbable vehicles to deliver and support processed particulate allogeneic bone as it is applied to defects such as excised cavities. These liquid or paste-like vehicles consist of a variety of polyhydroxy compounds, ester derivatives of polyols, hydrogels, and the like, sometimes containing additives to increase the viscosity of the vehicle (to retard dissipation of the vehicle and, thereby, extend the cohesiveness of the implanted mass) or factors to induce new bone growth. Anti-infective, anti-tumor and other additives also are described for these products. In no instances are these compositions indicated for, act as, or described in the art and claimed as bone hemostatic agents.

A. Bone Hemostasis

Attempts at providing absorbable bone hemostatic agents have not been completely successful. An absorbable bone sealant comprising fibrin and collagen (British Patent 1,584, 080) requires mixing in the operating room. A reportedly hemostatic dispersion of microfibrillar collagen in polyethylene glycol (U.S. Pat. No. 6,117,444) loses coherence too rapidly as the glycol is dissipated. A microcrystalline collagen lyophilized sponge (U.S. Pat. No. 6,454,787), designed for soft tissue hemostasis, is not as well-suited for bone bleeding control. A hemostatic agent employing polylactide (U.S. Pat. No. 4,186,448), lactide/glycolide oligomers (U.S. Pat. Nos. 5,143,730, 6,420,454), moldable polymer blends (U.S. Pat. No. 5,641,502), absorbable, hydrogel-forming synthetics (U.S. Pat. No. 6,413,539) are not easily adapted to bone hemostasis. Polydioxanone (U.S. Pat. No. 4,443,430) synthetic absorbable polymer materials are difficult to employ because of their relative instability in biocompatible, protonic delivery vehicles. Another absorbable polyester such as a. caprolactone polymer (U.S. Pat. No. 6,485,749) has been described as a replacement for bone wax.

A system with putty-like consistency at room temperature (U.S. Pat. No. 4,568,536), preferably combining a fatty acid salt, e.g., calcium stearate, an absorption enhancer, e.g., dextran and a vehicle, e.g., castor oil was developed as an absorbable, biocompatible matrix for the delivery of antibiotics, e.g., meclocycline sulfosalicylate, and other pharmacologically active agents to treat periodontal diseases. However, this technology, together with similar absorbable compositions described in U.S. Pat. No. 4,439,420 and U.S. Pat. No. 4,650, 665, are deficient because they are designed for drug delivery over extended absorption time periods not thought optimal for rapid bone healing and because they contain dextran, a polysaccharide presently believed to be a toxicologically unacceptable implant material.

B. Bone Defect Healing

Materials designed for bone defect healing (but not hemostasis) are based upon pulverized cortical and/or cancellous allogeneic, demineralized, osteogenic bone powder, having particle sizes usually between 1 and 12 mm, in a biocompatible carrier selected from the group consisting of polyols, e.g., glycerol and polyol derivatives, e.g., glycerol monoacetate (U.S. Pat. No. 5,073,373, U.S. Pat. No. 5,484,601). Many additives are cited for this composition, e.g., anti-infective and anti-tumor agents, surfactants, vitamins, endocrine tissue, etc. A variant of this technology (U.S. Pat. No. 5,284, 655) requires an increase of at least 10% in the volume of the demineralized bone component after contact with a swelling agent. The biocompatible suspending agent for the swollen demineralized bone particles is selected from the group including polyols and their esters, sucrose, polysaccharides, alginic acid, amylose, agar, etc. A further aspect of the U.S. Pat. No. 5,073,373 patent (U.S. Pat. No. 5,290,558) provides a flowable powder and claims large numbers of natural and synthetic polyhydroxy materials and their ester derivatives as vehicles for demineralized bone powder with a variety of additives such as BMP, IGF-1, anti-infective agents, hydroxyapatite, surfactants, bioerodable polymers and a variety of thickening agents such as PVA, PVP, CMC, gelatin, dextran, collagen, polyacrylate salts, etc. To improve handling characteristics of bone defect fillers (U.S. Pat. No. 5,314,476), particularly implant adhesion after the suspending vehicle is dissipated, demineralized bone particles of relatively high (10:1) median length to median thickness ratios are suspended in vehicles cited in the '558 patent. In an entirely different approach (U.S. Pat. No. 6,030,635), powdered demineralized bone carriers, based upon aqueous solutions of polyelectrolytes such as sodium hyaluronate, chitosan and N,O-carboxymethyl chitosan, are claimed. These viscous, high molecular weight hydrogels may contain anti-infective and other additives. A variant of U.S. Pat. No. 6,030, 635 (U.S. Pat. No. 6,437,018) includes the addition of a sodium phosphate buffer to form a more viscous hydrogel carrier for smaller particle sizes of mineralized or demineralized bone.

A recently issued patent (U.S. Pat. No. 6,565,884) describes a composition based on suspended demineralized bone matrix in lecithin or in lecithin containing unsaturated triglycerides, e.g. corn oil. The product is said, to induce bone growth. However, it is probable that the surface-active composition may easily be washed away after implantation. In yet another attempt to provide a useful material to stimulate new bone formation (U.S. Pat. No. 6,576,249), methods are described in which demineralized bone matrix is dissolved in water to form a viscous solution to which is added mineralized or demineralized bone matrix particles that form a water soluble, gel-like suspension.

As mentioned previously, in a search for a system to act as a matrix for the controlled delivery of various drugs, primarily for the treatment of periodontal diseases, workers developed absorbable, biocompatible, putty-like compositions that adhered to bone (teeth), were conformable at room temperature and easily applied (U.S. Pat. No. 4,568,536). While the primary objective of this composition was for prolonged drug delivery, the system was based largely upon earlier disclosed putty-like compositions specifically developed as bone hemostatic agents (U.S. Pat. No. 4,439,420).

The compositions described in U.S. Pat. No. 4,439,420 are based essentially upon combinations of three types of materials, a fatty acid salt, preferably calcium stearate, a fluid base, preferably castor oil, and an absorption accelerator, preferably dextran. This preferred composition, when tested for absorbability as an intramuscular implant, was described as taking approximately four weeks to absorb. No information or data concerning efficacy as a hemostatic device were presented and apparently no experiments were done to determine the absorption rate of the material when actually used as a bone hemostatic device. Absorption from the enclosed interstices of bone trabeculae would be expected to be significantly slower than absorption from the more anatomically "open" intramuscular site used as a model.

The U.S. Pat. No. 4,439,420 patent discloses alternatives for the three preferred ingredients. Alternatives to calcium stearate are magnesium, zinc, aluminum, lithium and barium salts of saturated and unsaturated fatty acids containing from 10 to 22 carbon atoms (collectively, fatty acid salts). Alternatives to castor oil are ethylene oxide/propylene oxide block copolymers, polyethylene glycols, methoxy polyethylene glycols, triglycerides, fatty acid esters, sesame oil, almond oil, cottonseed oil, corn oil, olive oil, cod liver oil, safflower oil and soya oil (collectively molecules which, admixed with the fatty acid salt, form the slowly absorbable putty-like mass). Alternatives to dextran are Carbowax®, the Pluronics®, glycerine and propylene glycol, which act as absorption accelerators by post-operatively absorbing fluids and/or dissipating, thereby physically disrupting the implant mass as it resides in tissue.

The primary reasons the U.S. Pat. No. 4,439,420 putty-like compositions are unsuited for bone hemostasis are that the material, while eventually biodegradable, is absorbed too slowly and, thus, inhibits new bone growth infiltration and healing by acting as a physical barrier, much as do the non-absorbable, paraffin-based bone waxes. In addition, the preferred composition described in the patent contains a component, i.e., dextran, which is not acceptable toxicologically. Finally, U.S. Pat. No. 4,439,420 compositions are "completely free of fibrous materials" which may be a significant disadvantage for optimum osteogenesis, a desirable characteristic for a bone hemostatic device. The addition of agents such as demineralized bone, bone growth factors and fibrous collagen to enhance osteogenesis and healing and anti-infectives to inhibit infection are not disclosed in the U.S. Pat. No. 4,439,420 patent.

BRIEF SUMMARY OF THE INVENTION

The formulations of the present invention are compositions having various viscosities and cohesive strengths and include putty and non-putty formulation consistencies.

The term "putty" is used herein as it is used in the art and is generally known to the skilled artisan. Dough (such as pastry dough), modeling clay, and glazier's putty of varying viscosities, depending on the indications and ultimate use, are examples of the consistency of a suitable product. Putties of various viscosities useable in the invention include those that are capable of adhering to bone. In general, putties which are soft, moldable, preferably non-elastic, cohesive mixtures prepared from a finely powdered substance intimately admixed with a liquid dispersing vehicle and having a shape which is capable of being deformed in any direction, are suitable consistencies for the putty-like compositions of the invention. As will be described later, however, compositions which have lower cohesive strengths than the putties described above, are within the scope of the invention, and may be used in specific applications in which the more viscous, higher cohesive strength putties are less suitable. For purposes of this invention, a major difference between putties of the invention and materials not considered to be putties (i.e. non-putties), but which are still within the scope of the invention, is that the non-putties have lower cohesive strengths than the cohesive strengths of the putty formulations. Individual non-putties of the invention are characterized by having the cohesive strength of creams, pastes, ointments, lotions, foams, gels, whipped egg whites, whipped cream, and the like. Preferably, the non-putties have only a fraction of the cohesive strength of putties of the invention, tending to be easily collapsible or easily torn apart under small stresses that would not, generally speaking, have the same effect on putties. The description which follows is given mainly in the context of the putties of the invention, it being understood, however, that if less cohesive strength materials are desired, the skilled artisan will simply make the appropriate changes in the proportions of components or add other substances to achieve the same purpose.

The present invention involves formation of medically useful absorbable putty-like and non-putty-like compositions using dispersing vehicles not previously reported for preparing such materials, intimately admixed with finely powdered bulking agents, some of which have been previously used, but not with the present dispersing vehicles, and some of which have not heretofore been used, in preparing such putty-like and non-putty-like compositions.

A sterile, absorbable bone hemostatic agent, that is, a material that will provide virtually immediate surgical hemostasis and also will absorb in the body after a relatively short period of time without compromising hemostasis efficacy, would have significant medical advantages over presently available materials. It would minimally inhibit osteogenesis and subsequent bone healing. Moreover, bone-healing adjuvants such as growth factors, particularly, for example, platelet derived growth factor (PDGF) and/or bone morphogenic proteins (BMPs) and others, could be added to the formulations to stimulate the bone healing process. Furthermore, adding agents such as oollageh, demineralized bone matrix (DBM), and/or hydroxyapatite could make the hemostatic material beneficially osteoconductive and osteoinductive. The addition of a suitable anti-infective agent such as antibiotics typified by tobramycin and gentamicin or bacteriostatic and bacteriocidal materials such as iodine, silver salts, colloidal silver, or the like serve to reduce the potential for infection, particularly in contaminated open wounds such as compound fractures. The addition of colorants would aid in visibility during the operative procedure. The addition of radiopaque substances allows the observation of post-operative sequelae using radiography. The addition of chemotherapeutic agents or radionuclides is useful when the putty is used, for example, in bone cavities arising from tumor resection. Analgesic compounds to reduce pain, and vasoconstrictors and blood clot-inducing agents to reduce hemorrhage, are useful additives.

The novel and inventive concepts described below for the preparation of the products of the present invention include at least two components, Component 1 being a bulking agent and Component 2 being a dispersing vehicle which, when intimately admixed with the bulking agent in appropriate proportions, yields a base for products of the invention. The selection of a suitable Component 2 will result in a composition that is absorbed by the body within an acceptable period of time. In such a case, Component 2 will act as its own absorption accelerant and the formulation will not require a separate absorption accelerant. If desired, however, the composition of the invention also may be provided with an optional ingredient which serves to accelerate the absorption of the putty by the body.

The invention provides implantable, appropriately absorbable, biocompatible, putty-like compositions that are useful as mechanical hemostatic tamponades for the control of osseous hemorrhage arising from surgical intervention or trauma and for providing an osteoinductive matrix to foster improved bone healing.

Accordingly, one aspect of the invention provides sterilizable putty-like compositions of matter and methods for their use comprising the step of physically pressing the putty-like compositions into the bleeding area of bone, thus mechanically staunching bleeding, after which the composition is absorbed and harmlessly eliminated from the body.

In another aspect, particularly useful in, but not necessarily limited to, traumatically opened wounds, an anti-infective agent is added to, and then post-operatively released from, the putty-like composition to inhibit the occurrence of postoperative infection.

In another aspect, the invention provides for adding to the art-known non-absorbable or slowly absorbable bone hemostatic materials, one or more of mineralized or demineralized bone particles, collagen, hydroxyapatite, bone morphogenic protein and/or other bone growth factors to form a novel putty-like composition for the dual purpose of providing initial hemostasis and then stimulating new bone formation.

In another aspect, the invention provide for the addition of an anti-infective agent to the putty-like composition containing bone growth stimulating additives to inhibit the occurrence of postoperative infection.

The anti-infective agent, which may be an antibiotic, a bacteriostatic or a bacteriocidal material, may be added to the putty-like mass or may be reversibly bound to additives, e.g. gelatin or collagen, which are to be contained within the putty. For example, using iodine as the anti-infective agent, a complex of iodine with gelatin, collagen or PVF may be used. In addition, colloidal silver, silver salts, or silver complexes with gelatin or other polymers may be used. Still further, antibiotics, in addition to being capable of being added to the putty as described above, may be added as part of a delivery system, preferably as part of a component of the putty. In particular, gentamicin, bound to powdered collagen, is an example of a useful antibiotic release system. Similarly, anti-neoplastic agents may be added to the putty-like composition in the same manner, preferably as a free agent, to provide an effective anti-tumorigenic material. Analgesics to reduce pain, blood clot-inducing agents to act as chemical hemostatic agents, and anti-inflammatory agents, may also be added. Furthermore, radiopaque components may be added to allow radiographic observation and colorants to improve intra-operative performance.

Additional objects, features and advantages will be apparent in the written description that follows.

DETAILED DESCRIPTION OF THE INVENTION

The compositions of the present invention include compositions comprising at least two and preferably three, four, or more components. They are most preferably body absorbable. In many embodiments they have a putty-like consistency. In one embodiment, the compositions are mechanically hemostatic tamponades useful in stopping the bleeding of bone by the application of the putty-like composition to the affected area. By "mechanically hemostatic tamponades" is meant that the compositions function by mechanically compressing the bleeding areas of the bone to arrest hemorrhaging as opposed to functioning by chemically hemostatic means, i.e. the arresting of hemorrhaging, in whole or in part, using a chemical means. In another embodiment, the compositions, in addition to being mechanically hemostatic, are also osteogenic in that they contain an added ingredient, i.e. a bone growth-inducing material, to aid in the induction of bone growth. Of the at least two components mentioned in the first sentence of this paragraph, Component 1 is a finely powdered bulking material having an average particle size sufficiently small to form a putty-like consistency when intimately admixed with the second component, i.e. dispersing vehicle Component 2 of the invention. Illustrations of Component 1 are hydroxyapatite, a carboxylic acid salt, preferably a fatty acid salt such as calcium stearate or a homolog thereof such as calcium laurate, or other finely powdered agents, such as synthetic absorbable polymers, e.g. polyglycolide, polylactide, co-polymers of lactide and glycolide, polydioxanone, polycaprolactones, as well as absorbable glasses, (such as those based upon phosphorus pentoxide and the like). The Component 2 dispersing vehicle is a liquid which, when intimately admixed with Component 1, enables the formation of the putty-like implant. While the two-component compositions of the invention provide the basic characteristics of suitable hemostatic materials as described herein, they may also, but are not required to, contain, if desired, optional ingredients 3 through 12, shown below. For example, optional Component 3 is an absorption accelerator, and Optional Component 4 is a bone growth-inducing material. Other components may be added to provide additional attributes to the putty-like and non-putty like compositions of the present invention as will be explained in more detail below.

Following is a detailed description of the various components.

Component 1

Component 1 is comprised of a finely powdered, preferably micronized, biocompatible, body-absorbable substance which, when admixed with a liquid dispersing vehicle, Component 2, forms the compositions of the invention. Suitable compositions are obtained when the average particle sizes of Component 1 materials are about 50 microns or less, but the preferred average particle size range is between about 3 to about 25 microns and most preferably about 6 to about 15 microns especially when putty-like compositions are desired. Particle sizes for non-putty compositions may range higher than those of the putty compositions, if desired.

Examples of one set of materials suitable for use herein are salts of one or more carboxylic acids having a carboxylate anion and a metal cation, some which are known in the art, having been described in U.S. Pat. Nos. 4,439,420 and 4,568,536. Suitably, the salts may be the calcium, magnesium, zinc, aluminum, lithium or barium salts of saturated or unsaturated carboxylic acids containing about 6 to 22 carbon atoms in the chain and preferably 8 to 20 carbon atoms. The preferred saturated carboxylic acids supplying the carboxylate anion may be selected from aliphatic acids such as caprylic acid, capric acid, lauric acid, myristic acid, palmitic acid, stearic acid, arachidic acid, and intervening homologs thereof, but the most preferred acids are the higher fatty acids such as lauric, myristic, palmitic, and stearic acids, with stearic being most preferred. Calcium and aluminum palmitates and stearates are preferred salts with calcium stearate being most preferred because of its excellent safety profile, and putty-forming characteristics. However, aluminum stearate, aluminum palmitate, or aluminum laurate, are suitable as well.

Examples of suitable unsaturated aliphatic acids which may be used for supplying the carboxylate cation are oleic acid and linoleic acid for which the same cations described above are used.

It has been discovered that finely divided materials, for example, about 50 microns or less, other than carboxylate salts, can be effective Component 1 substances. For example, it was surprising to find that finely powdered hydroxyapatite (calcium phosphate), especially when less than about 25 microns in average particle size, formed an excellent putty, especially with tocopheryl acetate as the liquid dispersing agent (Component 2). Furthermore, other materials, some of which are discussed in connection with Component 4, are useful as Component 1 when provided in finely powdered form. Examples of these are demineralized bone matrix (DBM), mineralized bone matrix (MBM), insoluble absorbable collagens, gelatin derived from collagens, monosaccharides, and polysaccharides. It is thought that any biocompatible material, when converted to very small particle sizes, will form medically useful compositions. It would not be uncommon, when producing compositions of the present invention, to have, for example, hydroxyapatite particles of 6-12 microns as Component 1, a suitable Component 2, with or without a suitable component 3 such as gelatin, and bone chips such as a demineralized bone matrix or a mineralized bone matrix having a particle size of about 0.5 to about 1 mm or larger as Component 4. Other examples are finely milled synthetic absorbable homo-, and co-polymers, e.g., polyglycolide, polylactide, copolymers of lactide and glycolide, polydioxanones, polycaprolactones, copolymers of dioxanone and of caprolactone and of trimethylene carbonate, gelatins, monosaccharides such as glucose and mannose, and polysaccharides such as carboxymethyl cellulose and oxidized cellulose typified by Surgicel®, starches, sucrose, suitably in the form of confectioner's sugar, alginic acid, hyaluronic acid, chitosan and its acetyl derivatives, and the like, as well as absorbable glasses, and the like. In addition, certain biologically active materials such as bioglasses (discussed in more detail in connection with Component 4 below), which may not be considered as-absorbable in the usual sense, can be used in finely powdered form as Component 1. For example, absorbable polymers having an average particle size below about 25 microns will form a useful, stable absorbable hemostatic putty when mixed with, for example, tocopheryl acetate or the triglyceride oils, especially the castor oil, of U.S. Pat. No. 4,439,420. Thus, any natural or synthetic absorbable polymer that can be reduced to sufficiently small particle size will form a stable, absorbable putty if admixed with a suitable, compatible vehicle.

It also has been discovered that absorbable glasses, based upon phosphorus pentoxide (instead of silicon dioxide), and containing alkali or alkaline earth metal oxides such as sodium, potassium, calcium and magnesium oxides as the network polymer, are slowly dissolvable in aqueous media and can be used as Component 1. In addition, such compounds may be used as absorption accelerants, i.e., as Component 3, in which case, they may, but need not, be used in as finely powdered a form as when they are used as Component 1. U.S. Pat. No. 4,612,923 refers to the preparative prior art concerning these glasses as well as their application as additives for strength reinforcement and stiffness enhancement for synthetic absorbable surgical devices. When the 325 mesh glass described in Example 1 of U.S. Pat. No. 4,612,923 is further pulverized to average particle sizes below 50 microns, the resulting fine powder forms a medically useful absorbable putty when admixed with the vehicles described in U.S. Pat. No. 4,439,420 and in this specification. The rate of aqueous dissolution (absorption) of such glasses can be increased by increasing the proportion of alkali metal oxides and decreased by increasing the proportion of alkaline earth metal oxides.

This novel approach, discussed above, i.e., forming useful absorbable putties by drastically reducing the particle size of the bulking vehicle Component 1, overcomes many of the difficulties of the prior art, especially those of synthetic absorbable. polymers as bone hemostatic agents.

Component 2

As the second component, i.e., the material which is mixed with Component 1 to obtain the composition of the invention, there may be mentioned several classes of materials that have not been heretofore employed as dispersing vehicles for preparing medical putties. At the outset, it should be noted that Component 2 is biocompatible and preferably a liquid because the liquid form facilitates the admixture with Component 1 to form the putty or non-putty mass. It will be appreciated, however, that Component 2 may also be a solid if a liquid vehicle (a liquefying agent, as more fully discussed below) is used to act as a medium for Components 1 and 2.

To aid in understanding the terms used herein and to help differentiate this aspect of the invention from that of the prior art, it would, perhaps, at this point, be useful to emphasize the nature of the chemical entities referred to in this Specification by briefly reviewing relevant classical chemistry terminology to ensure the appropriate chemical distinctions are understood.

Carboxylic acids are substances defined by the attachment of an OH group to a carbonyl function through a covalent bond. As a result, carboxylic acids possess physical and chemical properties totally distinct from substances containing either the carbonyl functionality (e.g., aldehydes, ketones) or the hydroxyl functionality (alcohols). The same distinction holds true for substances containing both the carbonyl and hydroxyl groups not directly attached through a covalent bond, such as hydroxyacetone, which displays both ketone and alcohol properties, but not carboxylic acid characteristics. Carboxylic acids always combine a carbonyl and an OH group and have acidic characteristics, but the OH group does riot have the characteristics of the hydroxyl group of an alcohol. A monocarboxylic acid would, therefore, not be described as a monohydroxy compound. To illustrate this, consider acetic acid and ethanol which are both two-carbon compounds containing an OH group. In acetic acid, the hydrogen atom of the OH group is liberated as an ion in water, whereas in ethanol, the hydrogen atom of the hydroxyl group is not so liberated. Thus, carboxylic acids dissociate and form carboxylate salts with bases, e.g., calcium stearate, a distinctive property that clearly differentiates the OH group of carboxylic acids from the hydroxyl group of alcohols that do not dissociate to form salts with bases. Thus, it would be entirely incorrect to characterize a carboxylic acid as an alcohol, a monohydric alcohol, or some such term since it is, in no chemical sense, an alcohol. Nor could a polycarboxylic acid be referred to as a polyalcohol, or a polyhydroxy compound or a polyol simply because it contains carboxylic OH groups. Such groups are not characterized as alcohols. An example of these distinctions is illustrated by considering the well-known molecule, citric acid. This substance has three carboxylic groups and one hydroxyl group in the same molecule. Citric acid is a monohydroxy (monohydric) alcohol as well as a polycarboxylic acid. The fact that citric acid contains three carboxylic OH groups does not classify this monohydroxy compound as a polyhydroxy compound. Because of the major differences in reactivity, synthesis and reactions, in every textbook of organic chemistry, the chemistry of alcohols always is considered in a separate chapter from the chemistry of carboxylic acids.

Alcohols may be regarded either as hydroxyl derivatives of hydrocarbons or as alkyl derivatives of water. They are typified by the R—OH structure where R is an alkyl group. In contradistinction to the readily ionizable hydrogen atom of the carboxylic acid hydroxyl group, the R—OH hydrogen atom is virtually unionized in water. On this basis, aliphatic alcohols are considered neutral rather than acidic. One or more hydroxyl groups may be appended to a hydrocarbon moiety so that, for example, propane may have one hydroxyl group (propyl alcohol), two hydroxyl groups (propanediol or propylene glycol) or three hydroxyl groups (propanetriol or glycerol). Propylene glycol and glycerol are simple examples of polyols. Polysaccharides, such as hyaluronic acid, contain many hydroxyl groups on each monomer unit and are correctly termed polyols. Alcohols may have short alkyl chains such as methyl alcohol, ethyl alcohol, propyl alcohol, etc., or they may have longer alkyl chains such as lauryl alcohol, myristyl alcohol, etc. It is of critical importance to note that lauric acid ($C_{11}H_{23}COOH$, a fatty acid) and lauryl alcohol ($C_{12}H_{25}OH$, a fatty alcohol) are completely different molecules in oxidation state and functionality, even though they both contain twelve carbon atoms.

Esters are commonly derived from the reaction of a carboxylic acid with an alcohol and can be converted back to the original carboxylic acid and alcohol by hydrolysis. Thus, acetic acid and ethyl alcohol are combined in the esterification process to form ethyl acetate and water. The term fat (or vegetable or animal oil) is confined to esters of a variety of long chain saturated or unsaturated fatty acids with glycerine (glycerides). Oils, cited in the prior art as vehicles for preparing putty-like materials, are exclusively glycerides, e.g., castor oil, sesame oil, olive oil, etc., as well as simple fatty acid esters such as ethyl laurate. What never have been proposed in the prior art as vehicles for preparing putty-like substances, are free liquid fatty carboxylic acids such as the saturated caprylic acid and the unsaturated oleic acid. Most important, the use of esters of fatty alcohols with low molecular weight mono- or polycarboxylic acids, e.g., lauryl acetate (the ester of lauryl alcohol and acetic acid) are completely novel for the preparation of putty-like materials and are chemically distinct from the prior art cited ethyl laurate (the ester of lauric acid with ethyl alcohol).

Returning now to the description of the Components of the present invention, more particularly Component 2, the elements are more specifically described as follows:

As a first class of Component 2, there are one or more absorbable esters of a $C_8$-$C_{18}$ monohydric alcohol with a $C_2$-$C_6$ aliphatic monocarboxylic acid. The monohydric alcohols may be selected from $C_8$-$C_{18}$ alcohols such as octyl alcohol, decyl alcohol, lauryl alcohol, myristyl alcohol, stearyl alcohol, and intervening homologs thereof. The preferred alcohols are the higher aliphatics such as lauryl alcohol, myristyl alcohol, and stearyl alcohol. Illustrative of the useful esters formed with the $C_2$-$C_6$ monocarboxylic acids are lauryl acetate and myristyl propionate.

As a second class of Component 2, there are one or more absorbable esters of a $C_2$-$C_{18}$ monohydric alcohol with a polycarboxylic acid. The $C_2$-$C_{18}$ monohydric alcohols include, in addition to the $C_8$-$C_{18}$ alcohols described in the first class of esters there are the lower aliphatic, $C_2$-$C_8$, alcohols such as ethanol, propanol, butanol, pentanol, heptanol, hexanol, and octanol which yield the corresponding ethyl, propyl, butyl, pentyl, heptyl, hexyl, and octyl moieties. The polycarboxylic acids may be selected from malonic, succinic, glutaric, adipic, pimelic, suberic, azelaic, sebacic, maleic, fumaric, glutaconic, citric, malic acids, and esters of the hydroxy function, if any, of the esterified polycarboxylic acid, especially acetyl citric acid and acetyl malic acids. It will be obvious to those skilled in the art that many combinations of alcohol/acid esters may be selected from the above, but the preferred ones for use in the invention from the monohydric alcohol/polyacid esters are diethyl succinate, dioctyl succinate, triethyl citrate, tributyl citrate, and higher and lower homologs thereof, acetyl triethyl citrate, acetyl tributyl citrate and higher and lower homologs thereof, butyryl triethyl citrate, diethyl malate, di-pentyl malate, and acetyl diethyl malate, and higher and lower homologs thereof.

Another class of materials, suitable as Component 2, are the higher $C_8$-$C_{12}$ up to about $C_{30}$ and preferably liquid or liquefiable monohydric alcohols such as octanol and decanol. An especially surprisingly suitable embodiment of this class is the aromatic alcohol tocopherol (Vitamin E) in its optically active or racemic forms and in any of the alpha, beta, gamma or delta forms, as well as liquid tocopherol esters (sometimes referred to herein as tocopherol esters) with a $C_2$-$C_{10}$ aliphatic monocarboxylic acid, a polycarboxylic acid or mixtures thereof. Useful are the tocopherol esters such as acetates, butyrates, caproates, caprylates, caprates, and intervening homologs thereof, and polycarboxylic acid ester such as those mentioned in the previous paragraph, especially esters of succinic, citric, and malic acids, with succinate being preferred.

Another class of materials, useful as Component 2, are hydrocarbons having from about 10-14 carbons atoms. For example, decane and dodecane are suitable.

Another class of materials, useful as Component 2, are the liquid or liquefiable saturated or unsaturated, free carboxylic acids such as the non-esterfied fatty acids, oleic, linoleic, caprylic, capric, and lauric. In this class, the normally liquid, saturated fatty acids would be suitable but may not be desirable because of their unpleasant odor. Some low melting saturated free-fatty acid mixtures that form a lower-melting eutectic mixture which is liquid-at-room-temperature may also be suitable. One advantage of saturated free-fatty acids lies in their improved stability to radiation sterilization whereas the unsaturated acids, e.g.,. oleic, may require radiation sterilization in an oxygen-free container. Higher homologs of solid acids can also be used in admixture with Component 1 in the presence of a liquefying medium or other suitable component. Any compatible liquid may be used as long as it ensures the liquefaction of Component 2 and is biocompatible as well.

Another class of materials, useful as Component 2, are ethers of the simple dialkyl ether class and alkyl aryl ether class as well as cyclic polymers of alkylene glycol e.g., ethylene glycol, known as crown ethers, all having boiling points greater than about 80° C. such as di-n-butyl ether, di-n-hexyl ether, di-n-octyl ether, and unsymmetrical ethers such as ethyl hexyl ether, ethyl phenyl ether, and the like, or, block copolymers of ethylene oxide and propylene oxide in various ratios of ethylene oxide to propylene oxide and various molecular weights, preferably from 1000 to 10,000, (Pluronics®). They are available in liquid or solid form. Illustrative of suitable materials are those shown below in examples 42, 56, and 57. In addition to their suitability for use as a Component 2, they may also be used as an absorption accelerant (Component 3). They are available under the trade name Pluronics® from BASF Corp. Mt. Olive, N.J. 07828.

Another class of materials, useful as Component 2, are symmetrical and unsymmetrical dialkyl ketones and alkyl aryl ketones having boiling points greater than about 80° C. such, as methyl propyl ketone, diethyl ketone, methyl butyl kitone, ethyl propyl ketone, methyl pentyl ketone, and 2-octanone, 2-nonanone, 2-decanone, and methyl phenyl ketone.

Another class of materials useful as Component 2 are selected from a member of the group consisting of polyhydroxy compounds, polyhydroxy compound esters, solutions of polyhydroxy compound, and mixtures thereof, and fatty acid esters. Preferred among these are the liquid polyhydroxy compounds selected from the group consisting of acyclic polyhydric alcohols, polyalkylene glycols, and mixtures thereof. Specific examples of the foregoing are ethylene glycol, diethylene glycol, triethylene glycol, 1,2-propanediol, trimethylolethane, trimethylopropane, erythritol, pentaerythritol, polyethylene glycols, a liquid solution of a fatty acid monoester of glycerol such as glycerol monolaurate. Solids among the foregoing may be dissolved or dispersed in a suitable solvent medium such as propylene glycol, glycerol, monoacetin, diacetin, liquid polyethylene glycol, and mixtures thereof. As glycerides, there may be mentioned monoglycerides, e.g., glyceryl acetate, glyceryl stearate, homologs thereof; and the like, diglycerides such as glyceryl diacetate, glyceryl dicaprate, dibutyrate, dilaurate, and the like, and triglycerides such as olive oil, castor oil, almond oil, sesame oil, cottonseed oil, corn oil, cod liver oil, safflower oil and soya oil. It should be noted that the foregoing polyhydroxy compounds may also be used, if desired, as Component 3 absorption accelerants. If DBM powder is present in the formulation (e.g., Component 1) then the polyhydroxy compound may not be an acyclic polyhydric alcohol, non-reducing sugar, sugar alcohol, sugar acid, monosaccharide, disaccharide, water-soluble or water dispersible oligosaccharide, polysaccharide, polyalkylene glycol or mixtures thereof.

Finally, another class of materials used as Component 2, is the so-called un-substituted and N-substituted pyrrolidones, typical among the latter of which are the $C_1$-$C_{12}$ N-alkyl pyrrolidones such as methyl, ethyl, propyl, butyl, octyl and dodecyl substituents and especially N-methylpyrrolidone ("NMP"). These materials, as is the case with other Component 2 materials, may be used as the sole Component 2 in admixture with Component 1. Alternatively, they may also be used in that mixture with any other suitable materials including other Component 2 materials. The resulting composition, a paste, a gel, putty or any other form of the composition, for example, is useful in accordance with the teachings of this invention. It may also be the base composition to which other optional components, whether or not listed herein, may be added.

NMP is miscible with water as well as organic solvents such as ether, chloroform, benzene, ethyl acetate, etc. It has a very low order of toxicity with mice $LD_{50S}$ reported at 3.5 ml (iv), 4.3 ml (ip) and 7.5 ml (oral). Chemically, NMP is an aprotic, substituted, cyclic amide and has no hydroxyl groups.

There are several primary variations that could be considered utilizing NMP. First, it forms a suitable putty with any of the carboxylic acid salts or micronized Component 1, In addition, dilution of the putty with additional NMP would provide products with less viscous, more flowable, paste-like consistencies. It is likely that, by employing absorbable materials soluble in NMP such as lactide/glycolide or caprolactone copolymers, gel-like compositions would be attainable. The NMP, as well as other pyrrolidones, may also be diluted with other materials such as triethyl citrate to make putties, pastes and creams. If micronized lactide/glycolide, or any other material that makes a putty, such as some synthetic absorbables, dissolves appreciably in NMP, a gel or paste may result.

Because NMP is both water and lipid soluble, absorption rates may be easily controlled by the addition of more hydrophobic additives, such as tocopheryl acetate, to the NMP. Thus, for example, concentration gradients of NMP-tocopheryl acetate mixtures, used as Component 2, provide excellent means for controlling absorption rates of devices based upon this system.

Finally, the addition of small molecules, such as drugs, or large molecules, such as proteins, e.g., DBM and growth factors, provides a useful system for controlled drug delivery.

As a statement of general applicability, it should be noted that Component 2 materials which are liquid at room temperature are the preferred substances for Component 2, and since they are liquids, a liquefying agent is not necessary. Also useful as Component 2 substances, however, are compounds which are solid at room temperature. In such cases, especially when putties are desired, a solid Component 2 is converted to a liquid form before, during, or after admixture with Component 1 through the use of an absorbable biocompatible liquefying agent capable of liquefying, solubilizing a solid Component 2. By "liquefying agent" as used herein, is meant an agent, such as a suitable solvent, which can solubilize the solid, or any other agent even though the agent may not be considered a solvent in the usual sense of that term, or an agent which can liquefy the solid, such as heat, or which can disperse the solid in a liquid as a dispersion so as to aid in the formation of a homogenous putty, cream or paste-like mixture. The particular agent used will, of course, depend upon the nature of Component 2 used in the particular formulation. Suitable agents are materials similar to Component 2 though not precisely described herein as Component 2.

The foregoing novel concepts and compositions utilizing the esters of monoalcohols with the mono- or polycarboxylic acids described above, provide an absorbable bone hemostatic implant. The novel utilization of relatively low molecular weight, non-toxic and rapidly degradable simple esters such as diethyl succinate, triethyl citrate and lauryl acetate have been found to provide superior alternatives to the much higher molecular weight fatty acid triglycerides, e.g., castor oil, for Component 2. This aspect of the invention thus permits one to eliminate, if desired, both the art-known version of Component 2, i.e. hydrophobic, slowly absorbed esters such as the triglycerides typified by the ricinoleic acid triglyceride, castor oil, as well as by fatty acid esters such as isopropyl myristate and the need for the use of an absorption accelerant.

These art-known putty compositions containing the art-known Component 2 materials, such as those of U.S. Pat. No. 4,439,420 can, however, be used to obtain useful osteogenic bone hemostatic materials in accordance with another aspect of the invention. It has been discovered that, when it is desired to have a bone hemostatic composition having osteogenic properties albeit with slower absorption characteristics, the art-known composition may be improved by the addition of osteogenic materials, e.g., demineralized bone matrix (DBM), mineralized bone matrix (MBM), hydroxyapatite, or growth factors such as bone morphogenic protein (BMP) and platelet derived growth factor (PDGF), as will described below.

Component 3—Optional

The third component, usually a hydrophilic material, is optionally included as an absorption accelerant and may even be used to control the kinetics of absorption by physically assisting in the disintegration of the implanted mass. Accelerants used in the prior art may be used if they are not toxic or otherwise bioincompatible. One or a combination of such prior art compounds as Carbowax®, the Pluronics®, (See discussion under Component 2 supra and discussion below) and glycerine, propylene glycol, lecithin, betaine, and polyhydroxy compounds such as hyaluronic acid, carboxymethylcellulose and chitosan and its acetyl derivatives may be used as absorption enhancers in the compositions of the invention, with the above caveat. It is preferred, however, to use for this purpose, other materials which are swellable or soluble and absorbable, such as either soluble or insoluble, natural or synthetic polypeptides, exemplified by purified, powdered insoluble fibrillar, but swellable collagens, the more rapidly absorbable soluble tropocollagens such as Vitrogen® and the more rapidly absorbable cold and hot water soluble polypeptides, e.g. the gelatins. Lecithin and octylphenyl ethoxylates, such as Triton® X 100, may be used as biocompatible surfactants to aid in swellability. Polyvinylpyrrolidone and other soluble, absorbable polymers such as the block copolymers of ethylene oxide and propylene oxide discussed supra in connection with Component 2, and relatively hydrophilic polypeptides, e.g., polyaspartic acid, polyglutamic acid, and their salts are also functional in this context. Most preferably, the compositions of the present invention contain, as the third component, insoluble, fibrillar collagen, soluble collagen, gelatin, octylphenyl ethoxylates (e.g. Triton® X 100), the block copolymers of ethylene oxide and propylene oxide, polyvinylpyrrolidone or absorbable phosphorus pentoxide-based glasses or stable mixtures of the foregoing. Particle sizes in the range of about 200-500 microns produce suitable results although larger or smaller particle sizes may be employed depending on the desires of the end user. Gelatin, PVP and other polymers have been used in the demineralized bone art as thickening additives but not as absorption accelerants. The thickening properties of gelatin vary directly with the Bloom number of the gelatin. Gelatin having Bloom numbers ranging from 100-300 are suitable in the compositions of the invention, although values above or below those numbers may be employed if the resulting product is acceptable to the end user.

Illustrative of some suitable proportions of Components which produce compositions having the properties described above, are the following:

Component 1. From about 5 to 80%, preferably about 20 to 50% by weight of the final composition.

Component 2. From about 10 to 70%, preferably about 20 to 50% by weight of the final composition.

Component 3. From about 0 to 80%, preferably about 10 to 70% by weight of the final composition.

While the foregoing discussion has been presented largely in the context of materials having the consistency of a putty, in some applications it may be desired to have a relatively less viscous or less cohesive composition. For example, it may be desired to place the composition of the invention into a void in the bone (drilled or otherwise formed, e.g. hairline fractures) into which a putty of high viscosity can be applied only with difficulty. A less viscous form of the putty compositions of the invention would be a desirable alternative. All one needs to do is modify the proportions presented herein to allow for a higher liquid concentration or add a compatible liquid diluent to achieve this purpose. Using this approach, an injectable form of the material can be obtained as well. Other less cohesive strength, non-putty compositions, such as creams, ointments, gels, lotions, and the like previously referred to, may be prepared in the same manner.

Component 4—Optional

The products described above are suitable hemostatic products which also will allow the growth of bone at the bone wound site. Thus, they are osteoconductive. A desirable aspect of the invention is to make the hemostatic product osteoinductive as well, that is, to provide the product with Component 4, a bone growth-inducing material (osteogenic material) in an amount effective to induce bone growth. Thus, it has been found that the inclusion of osteogenic materials such as growth factors, e.g. Platelet Derived Growth Factor (PDGF), Transforming Growth Factor beta (TGF-beta), Insulin-Related Growth Factor-I (IGF-I), Insulin-Related Growth Factor-II (IGF-II), Fibroblast Growth Factor (FGF), Beta-2-Microglobulin (BDGF II), bone morphogenic protein (BMP), and combinations thereof stimulate osteogenesis to varying degrees. Other bone growth-inducing materials such as demineralized bone matrix (DBM), osteonectin, osteocalcin, osteogenin, and combinations thereof, mineralized bone matrix (MBM), and/or hydroxyapatite, a component of normal bone, as well as bioactive glasses, render the hemostatic product suitably osteogenic. Hydroxyapatite is an inorganic calcium phosphate mineral, prepared, among other ways, synthetically or from sea coral (from which all organic material has been removed), which has been demonstrated to support the rapid in-growth of new bone tissue. Bioactive glasses are finely powdered glass particles which are biocompatible. They are useful as bone implant materials. A line of bioglasses is available commercially as VITRYXX™ from Schott, GmbH, Mainz, Germany. According to the manufacturer, when implanted into the body, the surface remodels to form "hydroxy carbono-apatite" upon which bone repair cells are deposited and form new bone tissue.

When used, a suitable amount of osteogenic material to be added to the compositions of the present invention ranges from about 0.001 to about 60% depending upon the material and preferably about 0.001 to about 40% by weight. When used as Component 4, i.e., as an osteogenic material, it is preferred to use certain agents such as DBM or mineralized bone in the form of larger average particle sizes. Suitable larger average particle sizes are in the range of about 0.05 to 10 mm preferably about 0.1 to 5 mm and most preferably about 0.5 to 1 mm. However, the use of Component 4 in smaller or larger particle sizes or in higher or lower amounts will also be suitable if the requirements of the ultimate user are satisfied.

With regard to the relative amounts of osteogenic material to be used in a composition of the invention, one would use a bone growth-inducing effective amount, by which is meant material adequate in amount and average particle size to be osteoinductive in the composition. The amount used may vary depending upon the efficacy of the osteogenic agent and the average particle size of the material. For example, growth factors such as BMP, Platelet Derived Growth Factor (PDGF) and the like are effective in fractional weight percent concentrations, whereas effective amounts of DBM, mineralized bone matrix, and hydroxyapatite are usually in higher weight percent concentrations, e.g., about 10% to about 50% or higher, and preferably in somewhat larger average particle sizes than those used in Component 1.

The addition of the bone growth-inducing material improves not only the compositions of the invention, but also improves the prior art hemostatic formulations to yield novel compositions therewith. Such additions will render these hemostatic formulations osteogenic as well. It is believed that the presence of the osteogenic material will also improve osteoconductive properties because the relatively large particles tend to "open up" the putty structure, thus providing spaces into which induced bone may proliferate.

The type of prior art hemostatic formulations which will especially be improved by such addition are the ones disclosed in U.S. Pat. Nos. 4,439,420 and 4,568,536 each of which is incorporated herein by reference for all purposes. Thus, the present specification and claims are to be read as though the complete specification and claims of the aforementioned patents were reproduced herein verbatim. For purposes of convenience, the formulations of those patents may be generally characterized as comprising an absorbable hemostatic composition for use in the control of osseous hemorrhage, comprising: a component comprising a biocompatible fatty acid salt, the cation of said fatty acid salt being selected from the group consisting of calcium, magnesium, zinc, aluminum, lithium and barium and a component comprising a body absorbable biocompatible base selected from the group consisting of ethylene oxide/propylene oxide block copolymers, polyhydroxy compounds, polyethylene glycols and methoxypolyethylene glycols, triglycerides and fatty acid esters, and an optional absorption enhancing agent. Thus, in this aspect of the invention, the bone growth-inducing materials are added to the above prior art formulations to produce an osteogenic hemostatic material as well as an osteoinductive bone defect filling material.

Other Optional Ingredients

To any of the compositions described supra, may be added a pharmaceutically effective amount of an anti-infective agent, either alone or bound to a substrate to slow its release. Illustrative of such anti-infective materials are tetracycline, vancomycin, cephalosporins, and aminoglyco sides such as tobramycin and gentamicin, alone or bound to collagen, for example, and combinations of the foregoing, iodine, alone or as a PVP complex, colloidal silver, silver salts, alone or bound to a carrier such as gelatin, collagen, and the like.

Other materials, such as a blood clot-inducing agents, e.g., epinephrine, tannic acid, ferrous sulfate, and the double-sulfates of a trivalent metal and a univalent metal such as potassium aluminum sulfate and ammonium aluminum sulfate; anti-neoplastic agents such as methotrexate, cis-platinum, doxorubicin, and combinations thereof, radionuclides such as Strontium 89, and the like; analgesics such as benzocaine, lidocaine, tetracaine, fentanyl (a potent non-opioid), and the like, anti-inflammatory substances such as the non-specific ibuprofen and aspirin, or the COX-2 specific inhibitors such as rofecoxib and celeboxib; radiopaque substances such as iodo, compounds, e.g., ethyl monoiodo stearate available as Ethiodol® (Savage Laboratories), and barium salts such as barium stearate, may be added in to the formulations in amounts which are effective to achieve their therapeutic or diagnostic purposes. Depending upon the characteristics of the colorant selected, colorants such as gentian violet, D&C Violet #2, and D&C Green #6 are suitable.

In some embodiments of the invention, it may be desirable to intimately admix water with the compositions of the invention. The presence of a small amount of water, of the order of up to ten percent or more, aids in a variety of ways among which is changing the tactile quality of the composition. In this regard, the resulting compositions often impart a sensation of reduced coarseness over what may have existed in the compositions without the water addition. In some instances, it is desirable to provide a putty-like formulation or a less dense non-putty formulation having a cohesive strength less than that of a putty, such as a cream, a paste, or other such materials as previously set forth herein, based upon water or other aqueous liquids rather than on more hydrophobic vehicles. Bulking agents such as the metal fatty acid salts, e.g., calcium stearate and other non-wettable bulking agents described herein, are not wetted by water and do not provide putty-like (or less dense) compositions with water. We have found, however, that the treatment of the bulking agent with a small amount of surface-active material, e.g., lecithin, the Pluronics® such as Pluronic L-35®, renders the unwettable bulking agent sufficiently wettable to enable the preparation of a suitable fatty acid salt-water formulation when Component 2 is an aqueous vehicle. Suitable aqueous vehicles are water, saline, various biocompatible buffer solutions, various body fluids, such as blood, serum, blood component concentrates, and the like.

While the above putties have less resistance to irrigation compared with the putties prepared using more hydrophobic materials, they have applications in bone defect repair where more rapid disintegration of the implant is desired. Non-ionic, cationic, and anionic surfactants are suitable, although virtually any biocompatible surfactant may be used as exemplified by dodecyl trimethyl ammonium chloride, sodium lauryl sulfate, nonoxynol-9, the Tweens, e.g., polyoxyethylenesorbitan monolaurate, Tergitol-7, i.e., sodium heptadecyl sulfate, and the antimicrobial surfactant, 1-lauryl-3-ethyl-benzo-triazolium bromide, and the like. Non-putty-like compositions, such as creams, pastes, and the like, may be prepared by using additional quantities of water. This is especially useful during surgical procedures when it is desired to form a putty- or cream-like composition using blood instead of water.

The foregoing discussion relating to the use of blood clot-inducing agents in the present invention illustrates the embodiment wherein the compositions are capable of chemical hemostasis in use. That is, the addition of the styptic material to the compositions of the present invention, whether those compositions are mechanically hemostatic or not, yields compositions having the ability to act as chemical hemostatic materials. Thus, an already mechanically hemostatic putty can be made more efficiently hemostatic by adding the blood clot-inducing material. Similarly, a lower cohesive strength cream or paste, which may lack significant mechanical hemostatic properties, can be made hemostatic by the addition of the blood clotting material. An example of the latter is the application of a thin layer of a vasoconstrictor-modified paste of the invention to a bleeding acetabulum in hip surgery.

The components described above, when added together in suitable proportions, yield useful, putty-like and non-putty like agents having, to varying degrees, many favorable characteristics. Various combinations of the components may require different times and temperatures in the preparation process in order for the putty-like characteristics to develop. For example, some materials such as finely divided hydroxyapatite may take longer than other components to achieve the putty-like state. In general, the putty-like compositions of the present invention are absorbable within a reasonable time, usually within 30 days although absorption times may be extended to several months, or longer for some applications. They are moldable and shapeable by hand at ambient temperatures, handle well in presence of blood, and are washable with saline. They sometimes are tacky to the touch, but do not stick to any great degree to surgical gloves, wet or dry. They can be radiation sterilized when radiation-sensitive material such as DBM or certain antibiotics are not present.

The actual proportions of the materials selected will vary depending upon the materials themselves, the number of components used, and the use desired for the final putty composition. The user will be guided initially by the requirement for the desired viscosity, cohesive strength, and consistency to be obtained, i.e. compositions ranging from flowable liquid consistencies to consistencies of creams, pastes, ointments, gels, and the like to the more cohesive putty-like consistencies, while maintaining other characteristics desired in the ultimate use of the component.

The compositions described in this specification, when used surgically, must be sterile. All, except those noted below, are radiation sterilizable using, for example, a standard cobalt-60 radiation source and a nominal dose of 25 kGy. Exceptions are formulations containing radiation-sensitive additives such as demineralized bone matrix, bone morphogenic protein, certain antibiotics, unsaturated molecules such as oleic acid and the like. When such materials are used, sterility may be achieved by radiation-sterilizing the bulk putty-like material and aseptically adding the sterile radiation-sensitive additive followed by aseptic packaging.

The compositions described in this specification may be sterile or sterilizable and may be packaged in several formats. The packages themselves may be sterile or sterilizable. The compositions may be packaged as an amorphous (i.e., shapeless or having no definite shape) material such as a paste, cream, or putty, or in the shape of its container. They may be shaped generally as a parallelepiped or as a generally rounded form, examples of the former being small brick-shapes or slabs (in the shape of a stick of chewing gum), and examples of the latter being cylindrical-shaped, egg-shaped, or spherical-shaped products. Alternatively, when the application permits and the viscosity is suitable, the product can be packaged in a syringe-like or plunger-assisted dispenser expressable or extrudable through an orifice of appropriate cross section and shape. A mechanical assist device similar to that used for caulking may be included. Another package contains the product in a squeezable, deformable tube such as a toothpaste-type tube or a collapsible tube such as those used in caulking applications, with an orifice shaped and sized to dispense any suitable shape onto the surface to be treated. The package may comprise an outer barrier as an overwrap, for example, a peelable blister pouch, to allow aseptic delivery of the package to the sterile field.

The present invention also contemplates methods of use of the compositions of the invention. For example, one embodiment is the method of mechanically controlling the bleeding of bone by the application of an effective amount of any of the compositions of the invention to bleeding bone, wherein the composition has a sufficiently dense consistency, such as in the putty compositions of the invention. In such a case, the composition is a mechanical hemostatic tamponade.

Another embodiment of the method of use of the invention is the method of chemically controlling the bleeding of bone by the application of an effective amount of any of the compositions of the invention, wherein the composition contains a blood clot-inducing agent as heretofore set forth. In the case of putties, the composition is a chemical hemostatic tamponade. Mechanical hemostatic tamponades of the invention which also comprise a clot-inducing agent will act as both a mechanical hemostat and a chemical hemostat.

Another method of the invention is the method for inducing the growth of bone in a bone defect by applying an effective amount of any composition of the invention containing a bone growth-inducing agent, to the affected area of bone, especially when the composition includes a bone growth-inducing material such as DBM, mineralized bone matrix, bone morphogenic protein, hydroxyapatite, or the like.

Another method is the method for treating an infection in or around a bone by applying an effective amount of any composition of the invention containing an anti-infective agent, to the affected area of bone to be treated.

Another method is the method for destroying cancer cells in or around a bone by applying an effective amount of any composition of the invention containing an anti-neoplastic agent, to the affected area of bone which contains such cells.

Another method is the method for reducing pain from an area in or around a bone by applying an effective amount of any composition of the invention containing an analgesic agent, to the affected area.

Another method is the method for controlling inflammation in or around a bone by applying an effective amount of any composition of the invention containing an anti-inflammatory agent, to the affected area.

Another method is the method for assessing the status of an area in bone to which an implant has been applied by applying an effective amount of any composition of the invention containing a radiopaque agent, to the affected area and thereafter radiographically visualizing the area and making a determination of the status of the area.

Another method is the method for rendering wettable any of the bulking agents used in the invention which may be hydrophobic by treating the bulking agent with a cationic, anionic, or non-ionic surfactant and then making a water-based putty from the treated bulking agent using any source of liquid such as water itself, saline, or body fluids such as blood, serum, or the like.

Those skilled in the art will be aware of the manner in which the compositions are applied and the amount thereof. In some applications, large amounts of the tamponade may be used while in others only small amounts may be required or desired.

The methods and examples provided below are intended to more fully describe preferred embodiments of the invention and to demonstrate its advantages and applicability.

The following examples illustrate specific embodiments of the present invention.

EXAMPLE 1

In this example and in all subsequent examples, unless otherwise indicated, the composition was prepared by mechanical blending of all dry reagents first and thereafter adding gradually any liquid reagents. The composition was "worked" with a spatula at room temperature until the desired consistency was obtained. In some cases, if the material needed additional ingredients to improve the consistency, that material was added and the mixture continually kneaded or "worked" until the, desired putty-like consistency was obtained. The components are presented in parts by weight.

| | | |
|---|---|---|
| Component 1 | Calcium stearate | 4 g. |
| Component 2 | Tocopheryl acetate | 3 g. |
| Component 3 | Gelatin | 3 g. |

The sample yielded a putty-like mass with excellent water resistance, physical and hemostatic characteristics and water resistance properties, i.e., it resisted strongly attempts at washing it away under the force of flowing tap water.

EXAMPLE 1a)

By varying the proportion of the liquid components, the compositions of the present invention can be rendered into states of lower (i.e. more liquid) or higher (i.e. more rigid) viscosities. Illustrative of a lowered viscosity formulation is the following: to the putty formulation of Example 1 is added 3 g. of acetyl triethyl citrate. The resulting product has a cream-like consistency and may be applied, in appropriate circumstances, to bone as a hemostatic agent or as a delivery agent for a variety of additives such as drugs.

EXAMPLE 2

Partial replacement of calcium stearate with bone growth-inducing materials a)

| | | |
|---|---|---|
| Component 1 | Calcium stearate | 3 g. |
| Component 2 | Tocopheryl acetate | 3 g. |
| Component 3 | Gelatin | 3 g. |
| Component 4 | Hydroxyapatite (6-12 micron particle size) | 1 g. |

The resulting product is a putty-like mass with properties comparable to the product in Example 1. When a small amount of gentian violet sufficient to impart a discriminating light violet color is added to the above formulation, a colored product with the characteristics of the product of Example 1 is obtained.

b) Complete replacement of calcium stearate with hydroxyapatite.

| Component 1 | Hydroxyapatite (6-12 micron particle size) | 2 g. |
|---|---|---|
| Component 2 | Tocopheryl acetate | 2.5 g. |
| Component 3 | Gelatin | 2 g. |

The composition was allowed to stand at room temperature for 72 hours yielding a product that had the characteristics of the product of Example 1.

EXAMPLE 3

| Component 1 | Aluminum Palmitate | 5 g. |
|---|---|---|
| Component 2 | Tocopheryl acetate | 3 g. |
| Component 3 | Gelatin | 3 g. |

The resulting product is a putty-like mass with properties similar to those described for the product in Example 1.

EXAMPLES 3a), 3b), 3c)

The putty-like formulation of Example 3 is rendered into less viscous compositions by modifying the Example 3 formulation as follows:

| | | Ex. 3 | Ex. 3a | Ex. 3b | Ex. 3c |
|---|---|---|---|---|---|
| Component 1 | Aluminum Palmitate | 5 | 5 | 5 | 5 |
| Component 2 | Tocopheryl acetate | 3 | 4 | 6 | 8 |
| Component 3 | Gelatin | 3 | 0 | 0 | 0 |

Formulation 3a has the consistency of a soft putty.
Formulation 3b has the consistency of a thick cream much like cake icing.
Formulation 3c has the consistency of a slowly flowable composition much like cold honey.
Each of them can be applied to bone as a hemostatic agent.

EXAMPLE 4

| Component 1 | Calcium stearate | 5 g. |
|---|---|---|
| Component 2 | Tocopheryl acetate | 3 g. |
| Component 3 | Gelatin | 3 g. |
| Component 4 | DBM | 3 g. |

The resulting product has in addition to hemostatic properties of the product of Example 1, the additional property of osteoconductivity.

EXAMPLE 5

| | | 5 a. | 5 b. |
|---|---|---|---|
| Component 1 | Calcium stearate | 2 g. | 1.3 |
| Component 2 | Triethyl citrate | 1.6 g. | 0.98 |
| Component 3 | Triton ® X 100 | 0 | 0.02 |

The resulting product 5a, was putty-like and had physical characteristics similar to those of Example 1. Product 5b was also putty-like and is more rapidly absorbable than 5a. Triton® X 100 is available from Dow Chemical Co., Midland, Mich.

EXAMPLE 6

| Component 1 | Calcium stearate | 4 g. |
|---|---|---|
| Component 2 | Triethyl citrate | 3 g. |
| Component 3 | Gelatin | 3 g. |

The resulting product was putty-like and had physical characteristics useful as a hemostat, but not preferred when compared to the product of Example 5.

EXAMPLE 7

| Component 1 | Calcium stearate | 2 g. |
|---|---|---|
| Component 2 | Acetyl triethyl citrate | 2 g. |

The resulting product has excellent putty-like characteristics and physical characteristics comparable to those of Example 1.

EXAMPLE 8

| Component 1 | Calcium stearate | 0.5 g. |
|---|---|---|
| Component 2 | Triethyl citrate | 1 g. |
| Component 4 | Hydroxyapatite | 2 g. |

There resulted a low viscosity injectable composition having hemostatic properties.

EXAMPLE 9

| Component 1 | Calcium stearate | .5 g. |
|---|---|---|
| Component 2 | Tocopheryl acetate | 2 g. |
| Component 4 | Hydroxyapatite | 2 g. |

There resulted a composition having excellent putty-like characteristics and water resistance.

EXAMPLE 10

| Component 1 | Hydroxyapatite | 2 g. |
|---|---|---|
| Component 2 | Triethyl citrate | 2.5 g. |

There resulted a composition which is easily applied to rough bone surfaces with good adhesion, and filling characteristics.

EXAMPLE 11

| Component 1 | Calcium stearate | 3 g. |
|---|---|---|
| Component 2 | Tocopheryl acetate | 1.0 g. |
| Component 2 | Triethyl citrate | 1.5 g. |
| Component 3 | Gelatin | 2 g. |

The resulting product was a good material with putty-like physical characteristics similar to those of Example 1 and somewhat more sticky than that of Example 1.

EXAMPLE 12

| Component 1 | Calcium stearate | 4 g. |
|---|---|---|
| Component 2 | Lauric acid | 4 g. |
| Component 2 | Tocopheryl acetate | .5 g. |

The calcium stearate was blended with melted lauric acid and formed a good putty which, upon cooling, solidified. The solid was then crushed and blended with the tocopherol to yield a good putty.

The resulting product has a putty-like consistency at body temperatures and a somewhat harder consistency at room temperature.

EXAMPLE 13

| Component 1 | Calcium stearate | 4 g. |
|---|---|---|
| Component 2 | Triethyl citrate | 4 g. |
| Component 2 | Lauric acid | 4 g. |

The resulting product was putty-like and had physical characteristics similar to those of Example 1 and with somewhat less cohesiveness.

EXAMPLE 14

| Component 1 | Calcium stearate | 2 g. |
|---|---|---|
| Component 2 | Dodecane | 1 g. |

The resulting product had good water resistance, was of lower viscosity and compared well with the other physical characteristics of Example 1.

EXAMPLE 15

| Component 1 | Calcium stearate | 2 g. |
|---|---|---|
| Component 2 | Octanol-1 | 1 g. |

The resulting product was of lower viscosity and had physical characteristics similar to those of Example 14 but somewhat less cohesive.

EXAMPLE 16

| Component 1 | Calcium stearate | 2 g. |
|---|---|---|
| Component 2 | Diethyl succinate | 2 g. |
| Component 3 | Gelatin | 2 g. |

The resulting product was a good putty similar to Example 1.

EXAMPLE 17

| Component 1 | Calcium stearate | 4 g. |
|---|---|---|
| Component 2 | Diethyl succinate | 3 g. |

The resulting product was a good putty which had improved consistency over that of Example 16.

EXAMPLE 18

| Component 1 | Calcium stearate | 4 g. |
|---|---|---|
| Component 2 | Acetyl triethyl citrate | 3 g. |
| Component 3 | Gelatin | 3 g. |

The resulting product was comparable to that obtained in Example 1.

EXAMPLE 19

| Component 1 | Aluminum palmitate | 4 g. |
|---|---|---|
| Component 2 | Tocopheryl acetate | .3 g. |
| Component 2 | Triethyl citrate | 3 g. |

The resulting product was a soft, somewhat translucent putty with good water resistance and good hemostatic characteristics.

EXAMPLE 20

| Component 1 | Calcium stearate | 3 g. |
|---|---|---|
| Component 2 | Tocopheryl acetate | 3 g. |
| Component 3 | Gelatin | 3 g. |
| Component 4 | Demineralized bone matrix | 1 g. |

The resulting product is a putty-like mass with properties comparable to the product in Example 1 and has osteogenic properties as well.

EXAMPLE 21

| Component 1 | Hydroxyapatite | 3 g. |
|---|---|---|
| Component 2 | Tocopheryl acetate | 3.5 g. |
| Component 3 | Gelatin | 3 g. |

In this example, the material initially was soft and oily and lacked coherence. However, upon standing at room temperature for 72 hours, an excellent putty with good water resistance formed. Increasing the amount of tocopheryl acetate by an additional 3 g. yields a paste having a coarseness attributable to the gelatin.

EXAMPLE 22

| Component 1 | Calcium stearate | 3 g. |
|---|---|---|
| Component 2 | Di-n-hexylether | 2.5 g. |
| Component 3 | Gelatin | 2 g. |

The resulting product is putty-like and has good water resistance and physical characteristics similar to those of Example 1.

EXAMPLE 23

| Component 1 | Calcium stearate | 3 g. |
|---|---|---|
| Component 2 | Di-n-pentylketone | 2.5 g. |
| Component 3 | Gelatin | 2 g. |

The resulting product is putty-like and has good water resistance and physical characteristics similar to those of Example 22.

EXAMPLE 24

| Component 1 | Calcium stearate | 3 g. |
|---|---|---|
| Component 2 | Tocopheryl acetate | 3 g. |
| Component 3 | Bovine collagen (powdered) | 3 g. |

The resulting product is putty-like, has good water resistance and physical characteristics similar to those of Example 23. In addition, the putty has a fibrous texture as a result of the fibrous powdered collagen sponge additive present as the absorption accelerator (Component 3).

EXAMPLE 25

| Component 1 | Calcium stearate | 3 g. |
|---|---|---|
| Component 2 | Tocopheryl acetate | 3 g. |
| Component 3 | *Bovine collagen (powdered) containing gentamicin sulfate. | 3 g. |

*CollatampG, available in Europe

There results a hemostatic putty with anti-infective properties.

EXAMPLE 26

| Component 1 | Calcium stearate | 4 g. |
|---|---|---|
| Component 2 | Tocopheryl acetate | 3 g. |
| Component 3 | Gelatin | 3 g. |
| Anti-Infective | Gentamicin sulfate | 120 mg. |

Example 1 is repeated except that 120 mg. of gentamicin sulfate is combined with the dry components before the tocopheryl acetate is added to make a putty. This example demonstrates the preparation of a putty with anti-infective properties.

EXAMPLE 27

| Component 1 | Calcium stearate | 4 g. |
|---|---|---|
| Component 2 | Tocopheryl acetate | 3 g. |
| Component 3 | Gelatin | 3 g. |

Example 1 is repeated except that the gelatin is soaked in 2% aqueous silver nitrate for 2 hours at room temperature, washed with two changes of distilled water and one of acetone and then dried overnight. This preparation has anti-infective properties as a result of the presence of silver/gelatin complexes.

EXAMPLE 28

| Component 1 | Calcium stearate | 4 g. |
|---|---|---|
| Component 2 | Tocopheryl acetate | 3 g. |
| Component 3 | Gelatin | 3 g. |

Example 1 is repeated except that 10 mg of the gelatin is incubated overnight in one ml. of an aqueous solution containing 10 micrograms of lyophilized human bone morphogenetic protein (BMP-2, Sigma-Aldrich) followed by air-drying overnight. The damp gelatin is washed with acetone to remove residual moisture and combined with the remainder of the gelatin to prepare the putty having osteogenic and hemostatic properties.

EXAMPLE 29

| Component 1 | Calcium stearate | 4 g. |
|---|---|---|
| Component 2 | Tocopheryl acetate | 3 g. |
| Component 3 | Gelatin | 3 g. |

Example 1 is repeated except that 0.5 ml of Betadine® (povidone-iodine, 10%; equivalent to 1% available iodine) was mixed into 10 g. of the formed putty of Example 1. The mass turned to a brown color and has anti-infective properties.

EXAMPLE 30

| Component 1 | Micronized polylactic acid | 3 g. |
| Component 2 | Tocopheryl acetate | 1.5 g. |

The mixture formed an excellent putty with good water resistance and properties comparable to the product in Example 1.

EXAMPLE 31

The following composition is described in U.S. Pat. No. 4,439,420 as a preferred composition of about 40% calcium stearate, 30% dextran and 30% castor oil. If water is added, the preferred composition is 38% calcium stearate, 28% dextran, 27% castor oil and 7% water (all weights are weight percent). The composition was prepared by mechanical mixing at ambient temperatures to avoid possible degradation of heat-sensitive components.

| Calcium stearate | 4 g. |
| Castor oil | 3 g. |
| Dextran | 3 g. |

The calcium stearate and dextran were dry blended in a 50 ml glass beaker and the castor oil was added with stirring using a spatula. After several minutes of "working" the mixture with the spatula at room temperature, the consistency gradually changed. The mixture became crumbly and, after further working, became putty-like. The addition of a small amount of water (about 1 g.) reduces the gritty nature of the dextran.

EXAMPLE 32

The formulation in Example 31 was modified as indicated below to make a novel, putty-like composition of the present invention. The mass is an effective hemostat and is an effective osteogenic bone defect filler.

| Calcium stearate | 2 g. |
| Castor oil | 1.5 g. |
| Dextran | 1.5 g. |
| DBM (demineralized bone matrix) | 1.5 g. |

The purpose of this example is to show that DBM can be added to the compositions described in U.S. Pat. No. 4,439,420 to obtain a putty-like mass with osteogenic properties.

EXAMPLE 33

| Component 1 | Aluminum Palmitate | 5 g. |
| Component 2 | Tocopheryl acetate | 3 g. |
| Component 3 | Gelatin | 3 g. |
| Additive | Methotrexate | .2 g. |

The now chemotherapeutic putty is packed into a bone defect following surgical excision of a bone tumor.

EXAMPLE 34

| Component 1 | Aluminum Palmitate | 5 g. |
| Component 2 | Tocopheryl acetate | 3 g. |
| Component 3 | Gelatin | 3 g. |
| Additive | Strontium 89 (as a salt) | |

The above formulation, when provided with radioactively effective amounts of Strontium 89, yields a radiotherapeutic putty as described in Example 33.

EXAMPLE 35

| Component 1 | Pulverized Absorbable Phosphate Glass | 3 g. |
| Component 2 | Tocopheryl Acetate | 1 g. |

A crucible containing sodium dihydrogen phosphate hydrate was heated for 4 hours at about 800 degrees C. and then rapidly cooled. The resulting absorbable phosphorus glass mass then was broken up with a hammer and the fragments pulverized to a fine powder in a rotating ball mill for about 72 hours. The finely pulverized glass (3 g.) was stirred with tocopheryl acetate (1.0 g.) until a putty-like mass formed having good physical properties and water resistance.

EXAMPLE 36

| Component 1 | Calcium stearate | 3 g. |
| Component 2 | Ethyl laurate | 3 g. |
| Component 4 | Demineralized bone matrix | 1 g. |

The purpose of this example is to show that DBM can be added to the compositions described in U.S. Pat. No. 4,439,420 to obtain a putty-like mass with osteogenic properties.

EXAMPLE 37

| Component 1 | Hydroxyapatite | 3 g. |
| Component 2 | Isopropyl palmitate | 3.5 g. |
| Component 3 | Gelatin | 3 g. |

Upon standing at room temperature for 72 hours, an excellent putty with good water resistance comparable to that of Example 2 is obtained.

EXAMPLE 38

| Component 1 | Calcium Stearate | 5 g. |
|---|---|---|
| Component 2 | Glycerol (USP) | 15 g. |

Three grams of calcium stearate were mixed with 3 gram incremental quantities of glycerol until the mixture displayed a cream-like consistency (total of 15 g. glycerol). At that stage, an additional two grams of calcium stearate were blended into the mixture to obtain a composition having the consistency and appearance of well-beaten egg whites.

EXAMPLE 39

| Component 1 | Calcium Stearate | 1 g. |
|---|---|---|
| Component 2 | Tocopheryl acetate | 1 g. |
| Component 3 | Glycerol | .25 g. |

There resulted a relatively soft putty with excellent water resistance.

EXAMPLE 40

| Component 1 | Sucrose (Confectioner's Sugar) | 3 g. |
|---|---|---|
| Component 2 | Olive Oil | 2 g. |

This results in a relatively rigid putty which washes away very easily and is useful where low water resistance is desired.

EXAMPLE 41

Three grams of the product from Example 38 above was mixed with 0.75 ml. of deionized water containing 30 ppm of colloidal silver (Source Naturals, Inc., Scotts Valley, Calif. 98006). The resulting hemostatic cream became off-white in color; due to the presence of the anti-microbial silver, and was somewhat less viscous than the original cream.

EXAMPLE 42

| Component 1 | Calcium Stearate | 4 g. |
|---|---|---|
| Component 2 | Pluronic ® L-35* (Molecular Wt. 1900) | 0.2 g |
| Component 12 | Water | 2 g |

*Pluronic 588310, Lot WPAW-502B, BASF, Corp. Mt. Olive, NJ 07828-1234

The ingredients are combined with stirring until a putty-like mass results. The material is easily dispersed in excess water.

EXAMPLE 43

| Component 1 | Calcium Stearate | 12.0 g. |
|---|---|---|
| Component 2 | d,l-alpha Tocopheryl Acetate | 7.5 g. |
| Component 3 | Soya Lecithin Granules | 1.3 g. |

The calcium stearate and lecithin (Archer-Daniels-Midland Ultralec P) were mixed dry and the tocopheryl acetate was then added with vigorous stirring. A putty formed which had good water resistance and handling properties, but which was slightly more tacky than corresponding formulations containing gelatin instead of lecithin.

EXAMPLE 44

| Component 1 | calcium stearate | 0.6 g. |
|---|---|---|
| Component 1 | potato starch* | 3.8 g. |
| Component 2 | d,l-alpha tocopheryl acetate | 1.6 g. |

*Razin International, Inc.
6527 Route 9
Howell, New Jersey 07731

The tocopheryl acetate and calcium stearate were mixed together and the starch was then added. The mixture formed a soft, white putty with good water resistance. To prevent the formation of post-operative adhesions, it may be desirable to sterilize the putty using 25 kGy of ionizing gamma radiation from a cobalt 60 source in order to degrade the starch. Alternatively, the starch may be subjected to radiation degradation prior to formulating it into the putty.

The following Examples 45-51 show putty compositions, prepared as in Example 1, having good water resistance and incrementally increasing absorbabilities from slowly absorbable to more rapidly absorbable as the amount of gelatin is increased relative to the amount of calcium salt.

|  | Parts Ca salt | Parts component 2 | Parts - | gelatin-% |
|---|---|---|---|---|
| EXAMPLE 45 | 12 Ca stearate | 7.5 tocopheryl acetate | 0 | 0 |
| EXAMPLE 46 | 12 Ca stearate | 7.5 tocopheryl acetate | 2.0 | 10 |
| EXAMPLE 47 | 12 Ca stearate | 7.5 tocopheryl acetate | 3.5 | 15 |
| EXAMPLE 48 | 12 Ca stearate | 7.5 tocopheryl acetate | 5.0 | 20 |
| EXAMPLE 49 | 12 Ca laurate | 7.5 tocopheryl acetate | 4.5 | 20 |
| EXAMPLE 50 | 12 Ca stearate | 7.5 triethy citrate | 4.5 | 20 |
| EXAMPLE 51 | 0.6 Ca stearate | 1.6 tocopheryl acetate | 5.0 | 70 |

-continued

|  |  |  | a) parts | % | b) parts | % |
|---|---|---|---|---|---|---|
| EXAMPLE 52 | Component 1 | Ca stearate | 3.4 | 31 | 2.35 | 21 |
|  | Component 2 | tocopheryl acetate | 3.2 | 29 | 2.21 | 20 |
|  | Component 3 | Gelatin (150 Bloom) | 4.4 | 40 | 3.04 | 28 |
|  | Component 4 | DBM | 0 |  | 3.40 | 31 |
|  |  | TOTAL | 11.0 |  | 11.0 |  |

The resulting product has characteristics similar to the putty of Example 53.

The gelatin in formulation a) is present at 40% by weight and the composition has good putty consistency with good water resistance and absorbability.

When it is desired to obtain a denser formulation that may be used as a vehicle in anchoring pins or screws, such as pedicle screws, to bone in orthopedic procedures, the foregoing formulation a) may be modified by including therein large particle size bone chips and applied to the appropriate bone site. Thus, when 31 parts of DBM, particle size 1-5 mm, are added to 69 parts of formulation a), formulation b) results, comprising 31% DBM and 28% gelatin. The consistency is that of a thick, dense putty into which pins or screws may be placed and anchored into adjoining bone. In time, the osteogenic character of the formulation will allow bone growth around the pins or screws thus permanently anchoring them to adjoining bone structures.

| EXAMPLE 53 | Component 1 | Ca stearate | 3.0 g |
|---|---|---|---|
|  | Component 2 | tocopheryl acetate | 0.4 g |
|  | Component 2 | tributyl citrate | 2.3 g |
|  | Component 3 | gelatin | 2.0 g |

There resulted a putty having very good hemostatic and absorbability characteristics.

| EXAMPLE 54 | Component 1 | Ca stearate | 3.0 |
|---|---|---|---|
|  | Component 2 | tocopheryl acetate | 0.4 |
|  | Component 2 | acetyl tributyl citrate | 2.3 |
|  | Component 3 | gelatin | 2.0 |

The resulting product has characteristics similar to the putty of Example 53.

EXAMPLE 56

| Component 1 | Calcium Stearate | 2.0 g. |
|---|---|---|
| Component 2 | Tocopheryl acetate | 1.5 g. |
| Component 3 | Pluronic ® F-38* (Molecular Wt. 4700) | 2.0 g. |

*Product 583095, Lot WP1W-515B, BASF Corp., Mt. Olive, NJ 07828-1234
The Pluronic was provided as a "Pastille" and ground to a powder before mixing. The mixture formed an excellent putty.

EXAMPLE 57

| Component 1 | Calcium Stearate | 4.0 g. |
|---|---|---|
| Component 2 | Pluronic ® L-35 (Molecular Wt. 1900) | 3.0 g. |

The Pluronic in this example was a viscous liquid and formed an excellent putty. Because this Pluronic is water soluble, it was not necessary to add an absorption accelerant.

EXAMPLE 58

| Component 1 | Calcium Stearate | 4.0 g. |
|---|---|---|
| Component 2 | N-methylpyrrolidone | 4.0 g. |
| Component 3 | Gelatin | 6.0 g. |

The mixture forms a suitable putty comparable to those containing tocopheryl acetate as Component 2.

EXAMPLE 59

| Component 1 | Calcium Stearate | 4.0 g. |
|---|---|---|
| Component 2 | N-methylpyrrolidone | 4.0 g. |
| Component 3 | Gelatin | 6.0 g. |
| Component 4 | DBM | 6.0 g. |

This composition is a thick putty having osteogenic properties.

The foregoing Examples are illustrative of specific embodiments of the present invention. Other embodiments, within the scope of the present invention, may be prepared by those skilled in the art as described in the foregoing Specification.

What is claimed is:

1. A body absorbable composition comprising in intimate admixture the following Components 1 and 2 wherein
    Component 1 is a finely powdered, carboxylic acid salt comprising a carboxylate anion and a metallic cation,
    Component 2 is a liquid block copolymer of ethylene oxide and propylene oxide.

2. The composition of claim 1 wherein the liquid block copolymer is a liquid at room temperature.

3. The composition of claim 1, wherein the liquid block copolymer comprises between 3 and 43 percent of the composition.

4. The composition of claim 3, further comprising tocopherol or tocopherol acetate in an amount of between 3 and 35 percent of the composition.

5. The composition of claim 1, wherein the carboxylate anion of Component 1 is an aliphatic acid selected from caprylic acid, capric acid, lauric acid, myristic acid, palmitic acid, stearic acid, arachidic acid, and intervening homologs thereof.

6. The composition of claim 5, wherein the carboxylate anion is stearic acid.

7. The composition of claim 1, wherein the metallic cation of Component 1 is calcium, magnesium, zinc, aluminum, or barium or mixtures thereof.

8. The composition of claim 7, wherein the carboxylate salt cation is calcium.

9. The composition of claim 4, further comprising an anti-infective agent.

10. The composition of claim 9, wherein the anti-infective agent is selected from tetracycline, vancomycin, cephalosporins, tobramycin, gentamicin, colloidal silver, and silver salts.

11. The composition of claim 3, wherein the composition is sterile.

12. The composition of claim 4, wherein the composition is sterile.

13. A method for mechanically controlling the bleeding of bone which comprises applying an effective amount of the composition of claim 3 to the affected area.

14. A method for mechanically controlling the bleeding of bone which comprises applying an effective amount of the composition of claim 4 to the affected area.

15. A package containing the composition of claim 3.

16. The package of claim 15, wherein the composition is sterile.

17. The package of claim 15, wherein the package is sterile.

18. The package of claim 15, wherein the composition is in an amorphous form or in a generally rounded form, or in a generally parallelepiped form.

19. The package of claim 15, wherein the package comprises a syringe-like or plunger-assisted dispenser containing the composition whereby said composition is expellable from said dispenser by the application of mechanical pressure applied to the plunger.

20. The package of claim 15, wherein the package comprises a squeezable, deformable tube containing the composition having an operable exit port whereby said composition is expellable from said tube by the application of mechanical pressure thereto.

21. The package of claim 15, wherein the package comprises an outer barrier to allow aaseptic delivery of the package into a sterile field.

* * * * *